US006372900B1

(12) United States Patent
Metallinos et al.

(10) Patent No.: US 6,372,900 B1
(45) Date of Patent: Apr. 16, 2002

(54) HORSE ENDOTHELIN-B RECEPTOR GENE AND GENE PRODUCTS

(75) Inventors: Danika Metallinos, Portola Valley; Jasper Rine, Moraga; Ann Bowling, Davis, all of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/175,658

(22) Filed: Oct. 20, 1998

Related U.S. Application Data

(60) Provisional application No. 60/062,562, filed on Oct. 21, 1997.

(51) Int. Cl.[7] ................................................. C12Q 1/68

(52) U.S. Cl. ......................................... 536/23.5; 435/6

(58) Field of Search ............................ 435/6; 536/22.1, 536/23.1, 23.5

(56) References Cited

PUBLICATIONS

Amiel, J. et al.; Heterozygous endothelin receptor B (EDNRB) mutations in isolated Hirschprung disease, Human Molecular Genetics, vol. 5, No. 3, pp. 335–337, (1996).
Anderson, D. Stem cells and transcription factors in the development of mammalian neural crest, FASEB Journal, vol. 8 pp. 707–713, (1994).
Auricchio, A. et al.; Endothelin–B receptor mutations in patients with isolated Hirschprung disease from a non–inbred population, Human Moecular Genetics, vol. 5, No. 3, pp. 351–354, (1996).
Badner, J. et al.; A Genetic Study of Hirschsprung Disease, Am. J. Hum. Genet. vol. 46, pp. 568–580, (1990).
Barsh, G., The genetics of pigmentation; from fancy genes to complex traits, TIG, vol. 12, No. 8, pp. 299–305, (1996).
Baynash, A, et al.; Interaction of Endothelin–3 with Endothelin–B Receptor is Essential for Development of Epidermal Melanocytes and Enteric Neurons, Cell, vol. 79, pp. 1277–1285, (1994).
Bowling, A.; Dominant Inheritance of Overo Spotting in Paint Horses, The Journal of Heredity, vol. 85, No. 3, pp. 222–224, (1994).
Bronner–Fraser, M.; Neural crest cell formation and migration in the developing embryo, FASEB Journal, vol. 8, pp. 699–705, (1994).
Ceccherini, I, et al.; Interstitial deletion of the Endothelin–B receptor gene in the spotting lethal (sl) rat, Human Molecular Genetics, vol. 4, No. 11, pp. 2089–2096, (1995).
Doel, M.; The relationship between abnormalities of pigmentation and of the inner ear, Birth Defects 16, pp. 243–261, (1970).
Haendler, B., et al.; Molecular Cloning of Human Endothelin (ET) Receptors $ET_A$ and $ET_B$, J. Card. Pharm. vol. 20, pp. s1–s10, (1992).

Hosada, K, et al.; Targeted and Natural (Piebald–Lethal) Mutations of Endothelin–B Receptor Gene Produce Megacolon Associated with Spotted Coat Color in Mice, Cell. No. 1. 79, pp. 1267–1276, (1994).
Kunieda, T., et al.; A Mutation in Endothelin–B Receptor Gene Causes Myenteric Aganglionosis and Coat Color Spotting in Rats, DNA Research vol. 3, pp. 101–105, (1996).
Kusafuka, T., et al.; Novel mutations of the endothelin–B recveptor gene in isolated patients with Hirschsprung's disease, Human Molecular Genetics, vol. 5, No. 3, pp. 347–349, (1996).
McCabe, L.; Overo Lethal White Foal Syndrome: Enquine Model of Aganglionic Megacolon (Hirschsprung Disease), Am. J. of Med. Genetics, No. 1. 36, pp–336–340, (1990).
Markland, L., et al.; A missense mutation in the gene for melanocyte–stimulating hormone receptor (MC1R) is associated with the chestnut coat color in horses, Mammalian Genome, vol. 7, pp. 895–899, (1996).
Metallinos, D. et al.; Fine Structure Mapping and Deletion Analysis of the Murine piebald Locus, Genetics, vol. 136, pp. 217–223, (1994).
Metallinos, D. et al.; A missense mutation in the endothelin–B receptor gene is associated with lethal White Foal Syndrome: an equine version of Hirschsprung Disease, Mammalian Genome, vol. 8, pp. 426–431, (1998).
Mizuno, T., et al.; Structure of the Bovine Endothelin–B Receptor Gene and Its Tissue–Specific Expression Revealed by Northern Analysis, Journal of Cardiovasc. Pharmacol., vol. 20, Supp. 12, pp. s8–s10, (1992).
Pavan, W., et al.; Piebald lethal ($s^1$) acts early to disrupt the development of neural crest–derived malanocytes, Proc. Natl. Acad. Sci., vol. 91, pp. 7159–7163, (1994).
Puffenberger, E., et al. A Missense Mutation of the Endothelin–B Receptor Gene in Multigenic Hirschsprung's Disease, Cell, vol. 79, pp. 1257–1286, (1994).
Rudolph, J., et al.; Periodic paralysis in Quarter Horses: a sodium channel mutation disseminated by selective breeding; Nature Genetics, vol. 2, pp. 144–147, (1992).
Saito, Y., et al.; Primary Structure of Bovine Endothelin ETB Receptor and Identification of Signal Peptidase and Metal Proteinase Cleavage Sites, J. of Biol. Chem. vol. 266, No. 34, pp. 23433–23437 (1991).
Santschi, E., et al.; Endothelin receptor B polymorphism associated with lethal white foal syndrome in horses, Mammalian Genome, vol. 9, pp. 306–309 (1998).

(List continued on next page.)

*Primary Examiner*—Eggerton A. Campbell
(74) *Attorney, Agent, or Firm*—Morrison & Foerster LLP (57) ABSTRACT

The horse endothelin-B receptor gene has been identified, isolated, purified, sequenced and mapped. The horse endothelin-B receptor gene is associated with Lethal White Foal Syndrome. A PCR based assay has been developed to identify a specific mutation in the endothelin-B receptor gene associated with Lethal White Foal Syndrome. The cDNA clone for the horse endothelin-B receptor has been isolated and purified. Molecular genetics probes for the horse endothelin-B receptor gene and gene products are presented.

19 Claims, 3 Drawing Sheets

OTHER PUBLICATIONS

Trommershausen–Bowling, A.; Equine linkage group II: phase conservation of To with $A1^B$ and $Gc^S$, J. of Heredity, vol. 78, pp. 248–250, (1987).

Trommershausen–Smith, A.; Lethal White Foals in Matings of Overo Spotted Horses, Theriogenology, vol. 8, No. 5, pp. 303–311 (1977).

Vonderfecht, S.; et al.; Congenital Intestinal Aganglionosis in White Foals, Vet. Pathol. No. 1. 20,. pp. 65–70, (1983).

Yang, G. et al.; A dinucleotide mutation in the endotholein–B receptor gene is associated with lethal white foal syndrome (LWFS); a horse variant of Hirschsprung disease, (HSCR), Human Molecular Genetics, vol. 7, No. 6, pp. 1647–1652; (1998).

```
              E1.F
wildtype      CAAATGCCTA AAGCAGGGAG GACGGCGGGA GCCCAGCGAC GCACCCTCCC
lethal white  CAAATGCCTA AAGCAGGGAG GACGGCGGGA GCCCAGCGAC GCACCCTCCC
                                  E1-2.F
wildtype      TCCTCCCCCG TGCGAAAGAA CCATCGAGAT CAAGGAGACT TTCAAGTACA
lethal white  TCCTCCCCCG TGCGAAAGAA CCATCGAGAT CAAGGAGACT TTCAAGTACA
                                                           lw2.F
wildtype      TCAACACAGT AGTGTCCTGC CTAGTGTTCG TGCTGGGCAT CATCGGAAAC
lethal white  TCAACACAGT AGTGTCCTGC CTAGTGTTCG TGCTGGGCAT CAAGGGAAAC
                                                         wt2.F
wildtype      TCCACACTGC TGAGAATCAT TTACAAGAAC AAGTGCATGC GGAACGGCCC
lethal white  TCCACACTGC TGAGAATCAT TTACAAGAAC AAGTGCATGC GGAACGGCCC
                                              E1.R
wildtype      TAATATCTTG ATCGCCAGCC TGGCTCTGGG AGACTTGCTG CA
lethal white  TAATATCTTG ATCGCCAGCC TGGCTCTGGG AGACTTGCTG CA
```

FIG._2A 174 bp Positive Control for the PCR Reaction (E1.F and E1.R)

105 bp Lethal White Specific Product (lw2.F and E1.R)

90 bp Wildtype Specific Product (wt2.F and E1-2.F)

HORSE ENDOTHELIN-B RECEPTOR GENE AND GENE PRODUCTS

RELATED APPLICATION

This application claims the benefit under 35 U.S.C. §119 (e) of United States provisional patent application No. 60/062,562, filed Oct. 21, 1997.

FIELD OF THE INVENTION

This invention relates to the field of molecular biology. In particular, this invention relates to horse endothelin-B receptor genes and gene products and methods of analysis of the genes and gene products.

BACKGROUND OF THE INVENTION

Coat color genetics plays an important role in mapping studies in mouse, rat and horse. Barsh, G. S. (1996) TIG Vol. 12, No. 8 299–305; Bowling, A. T., (1987) Journal of Heredity. 78: 248–250; and Marklund et al., (1996) Mammalian Genome 7: 895–899. Because coat color forms are desirable and selectable qualities in domestic species, variants are often preserved and recorded by a registry. The American Paint Horse Association registers Paint horses, as well as those thoroughbreds or offspring of Quarter Horse parents that are born with a white spotting pattern.

There are two distinct coat color patterns recognized by the American Paint Horse Association: tobiano and overo. Tobiano, inherited as an autosomal dominant trait, has been mapped to a linkage group containing Albumin and Vitamin D binding protein that is conserved in mouse and humans (Bowling, 1987). The overo inheritance pattern is not clearly defined and the map position has not been identified, perhaps because there are genetically different patterns registered as "overo". One particular pattern registered as overo is characterized by a variable pattern of jagged white markings predominantly localized to the lateral and ventral parts of the body and is referred to as "frame" overo. Other patterns registered as overo exist where all four legs and the head are white but there is little white on the lateral aspect of the horse. Clear distinction between patterns is not always possible from phenotype so these patterns have been registered as a single category (overo). Frame overos are the specific subset of overos that most frequently appear to produce foals that exhibit Lethal White Foal Syndrome. McCabe et al., American Jour. Med. Gen. 36:336–340 (1990); Trommershausen-Smith, Theriogenology 8(5):303–311 (1977); Vonderfecht et al., Amer. Jour. Med. Gen. (1983).

Lethal White Foal Syndrome is a disease in horses characterized by an all white coat and intestinal tract abnormalities that result in colic and related symptoms within 12 hours of birth. McCabe et al., (1990); Trommershausen-Smith, (1977); Vonderfecht et al., 1983). White foals with the disease die soon after birth. There is no known treatment or cure for this syndrome. Bowling, A.T. (1994) Journal of Heredity. 85 (3):222–224; McCabe, L., et. al. (1990) Amer. Jour. Med. Gen. 36:336–340; Vonderfecht, S. L., et al. (1983) Vet. Patho. 20: 65–70.

Diseases similar to Lethal White Foal Syndrome have been identified and genetically characterized in humans (Hirschsprungs Disease) Chakravarti, A. Human Molecular Genetics 5:3:303–307 (1996) and mice (*piebald lethal*). Metallinos, D. L., et al. (1994) Genetics. 136: 217–223. These diseases have been demonstrated to be caused by mutations in the endothelin-B receptor gene of humans and mice, respectively. The horse endothelin-B receptor gene has not been identified nor has it been shown to be related to Lethal White Foal Syndrome.

There is thus a need to identify and clone the Lethal White Foal gene in horses in order to identify carriers of the gene. In addition, there is a need to clone the horse endothelin-B receptor gene and to determine if mutations in the gene cause Lethal White Foal Syndrome. There is also a need to develop a molecular genetic test for Lethal White Foal Syndrome so that horses that have the potential to produce lethal white foals can be identified. There is a further need to place the gene for Lethal White Foal Syndrome on the horse genetic map so that it can be used as an anchor locus in the continued development of a horse syntenic map.

SUMMARY OF THE INVENTION

In order to meet these needs, the present invention is directed to the identification, isolation, cloning, sequencing, purification and mapping of the horse (Equine) wild type and mutant endothelin-B receptor (EDNRB) gene and cDNA.

This invention is also directed to molecular biological probes including DNA, RNA, cDNA, peptide, protein and antibody probes for horse EDNRB genes and gene products and mutant genes and gene products.

This invention is also directed to a PCR assay for the detection of EDNRB gene mutations in horses.

This invention is also directed to methods of in vivo and in vitro analysis of the expression of horse EDNRB wild type and mutant genes and gene products.

This invention is further directed to isolated oligonucleotides which include one or more nucleotide sequences and the corresponding complement nucleotide sequences selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 20, SEQ ID NO: 22, SEQ ID NO: 23, SEQ ID NO: 24 and SEQ ID NO: 25.

This invention is further directed to a polymerase chain reaction (PCR) kit which includes oligonucleotides such as one or more of: SEQ ID NO: 3, SEQ ID NO: 5, SEQ ID NO: 13, SEQ ID NO: 14 and SEQ ID NO: 15. The kit of the invention may further include reaction buffers and PCR DNA polymerase.

This invention is further directed to a method for determining the expression of the wild type and mutant horse endothelin-B receptor gene in a biological sample by nucleic acid hybridization. In the method of the invention, a nucleic acid probe including one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 20, SEQ ID NO: 22, SEQ ID NO: 23, SEQ ID NO: 24 and SEQ ID NO: 25 is utilized in hybridization reactions.

This invention is further directed to a method for identifying a horse wild type and mutant endothelin-B receptor gene by amplifying a portion of the endothelin-B receptor gene from a horse biological sample by using primers such as SEQ ID NO: 3, SEQ ID NO: 5, SEQ ID NO: 13, SEQ ID NO: 14 and SEQ ID NO: 15 in amplification reactions wherein the amplification results in the generation of 174, 105 and 90 nucleotide-long polynucleotides. The method of the invention further includes the step of detecting the presence of amplification products.

The invention is further directed to an isolated nucleotide sequence comprising the sequence shown in SEQ ID NO: 20. The invention is further directed to the nucleotide sequence shown in SEQ ID NO: 20 wherein the sequence is linked to a heterologous nucleic acid. In the invention, the heterologous nucleic acid may be a promoter and/or a vector which is capable of functioning in mammalian, microbial, plant or avian cells.

The invention is further directed to an isolated nucleic acid encoding the polypeptide of SEQ ID NO: 21.

The invention is further directed to purified or isolated peptides comprising the amino acid sequence shown in SEQ ID NO: 21, SEQ ID NO: 17 and SEQ ID NO: 19. The invention is further directed to isolated and purified polyclonal and monoclonal antibodies produced from the peptide sequences of SEQ ID NO: 21, SEQ ID NO: 17 and SEQ ID NO: 19.

BRIEF DESCRIPTION OF THE DRAWINGS

The invention will be better understood by reference to the figures, in which:

FIG. 1 shows horses exhibiting different white spotting patterns.

FIG. 2B shows the results of a PCR reaction run on a 12% polyacrylamide gel and stained with ethidium bromide. Lane 1 is the PCR product from a heterozygote horse sample; lane 2 is the PCR product from Lethal White Foal horse sample and lane 3 is the PCR product from a homozygous wild-type horse sample.

In FIG. 2B, each lane has the 174 base pair control for the PCR reaction resulting from amplification with primers E1.F (SEQ ID NO: 3) and E1.R (SEQ ID NO: 5). Lanes 1 and 2 have the 105 base pair lethal white specific product resulting from amplification with primers lw2. F (SEQ ID NO: 14) and E1.R (SEQ ID NO: 5). Lanes 1 and 3 have the 90 base pair wild-type specific product resulting from amplification with primers wt2.F (SEQ ID NO: 15) and E1–2.F (SEQ ID NO: 13).

FIG. 3 is a schematic diagram of the endothelin-B receptor protein. The gray area represents the plasma membrane. The cylinders numbered 1–7 represent the transmembrane domain of the protein. An asterisk marks the location of the missense mutation in the horse DNA sequence. Open circles mark the location of the missense mutations in human DNA sequences. The closed circle marks the location of the missense mutation identified in mice.

BRIEF DESCRIPTION OF THE SEQUENCE LISTING

SEQ ID NO: 1 is an oligonucleotide primer sequence that was generated based on the sequence conservation between bovine, mouse and human sequences for the endothelin-B receptor (EDNRB).

SEQ ID NO: 2 is an oligonucleotide primer sequence that was generated based on the sequence conservation between bovine, mouse and human sequences for EDNRB; a primer for EDNRB EXON 7 amplification and a primer for PCR analysis of the Lethal White Foal Allele.

SEQ ID NO: 3 is an internal primer for DNA sequencing of the horse EDNRB cDNA and a primer for PCR analysis of the Lethal White Foal Allele.

SEQ ID NO: 4 is an internal primer for DNA sequencing of the horse EDNRB cDNA.

SEQ ID NO: 5 is a primer for DNA sequencing of the horse EDNRB Exon 1 and a primer for PCR analysis of the Lethal White Foal Allele.

SEQ ID NO: 6 is a primer for DNA sequencing of the horse EDNRB Exon 2-Exon 3.

SEQ ID NO: 7 is a primer for DNA sequencing of the horse EDNRB Exon 2-Exon 3.

SEQ ID NO: 8 is a primer for DNA sequencing of the horse EDNRB Exon 4-Exon 5.

SEQ ID NO: 9 is a primer for DNA sequencing of the horse EDNRB Exon 4-Exon 5.

SEQ ID NO: 10 is a primer for DNA sequencing of the horse EDNRB Exon 6.

SEQ ID NO: 11 is a primer for DNA sequencing of the horse EDNRB Exon 6.

SEQ ID NO: 12 is a primer for DNA sequencing of the horse EDNRB Exon 7.

SEQ ID NO: 13 is a primer for DNA sequencing of the horse EDNRB PCR products.

SEQ ID NO: 14 is a primer for horse EDNRB PCR analysis.

SEQ ID NO: 15 is a primer for horse EDNRB PCR analysis.

SEQ ID NO: 16 is a horse EDNRB DNA sequence.

SEQ ID NO: 17 is a horse EDNRB protein sequence.

SEQ ID NO: 18 is a horse EDNRB DNA sequence.

SEQ ID NO: 19 is a horse EDNRB protein sequence.

SEQ ID NO: 20 is a horse EDNRB cDNA sequence.

SEQ ID NO: 21 is a horse EDNRB peptide sequence derived from the cDNA sequence in SEQ ID NO: 20.

SEQ ID NO: 22 is a horse EDNRB intron sequence.

SEQ ID NO: 23 is a horse EDNRB intron sequence.

SEQ ID NO: 24 is a horse EDNRB intron sequence.

SEQ ID NO: 25 is a horse EDNRB intron sequence.

DETAILED DESCRIPTION OF THE INVENTION

To ensure a complete understanding of the invention the following definitions are provided:

Endothelin-B receptor: The endothelin-B receptor (EDNRB) is a G-protein coupled seven membrane receptor for the endothelins. Endothelin-3, the predominant ligand for this receptor, is a 21 amino acid signaling molecule. Mutations in the gene encoding endothelin-3 cause sporadic Hirschsprung disease in humans and lethal spotting in mice. Both the endothelin-B receptor and endothelin-3 are essential for the normal development of the enteric ganglia and melanocytes.

Polymerase Chain Reaction: The polymerase chain reaction (PCR) is a technique utilized to amplify DNA. Typical PCR reactions include oligonucleotide primers, DNA polymerase and a mixture of oligonucleotide primers. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School. (1987) which is hereby incorporated by reference.

Oligonucleotide Primers: Oligonucleotide primers are short chains of nucleotides useful in PCR techniques, DNA sequencing and cloning methods.

Complementary Sequence: Oligonucleotides hydrogen bond to complementary oligonucleotides forming pairs such as Adenine-Thymine and Cytosine-Guanine. The complement sequence for an oligonucleotide sequence refers to the complementary (hydrogen bond pair) oligonucleotides for the particular oligonucleotide sequence.

Taking into account these definitions, the present invention is directed to methods, processes and compositions for identifying, isolating, cloning, sequencing, purifying and mapping the horse (Equine) wild type and mutant endothelin-B receptor (EDNRB) gene, cDNA and gene products. The EDNRB gene is related to Lethal White Foal Syndrome.

Figure 1A:
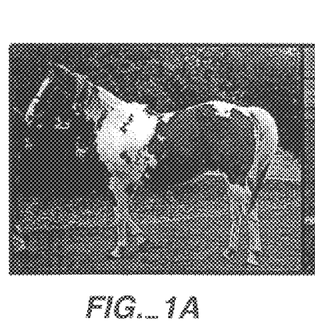
FIG. 1A shows a horse exhibiting a tobiano white spotting pattern.
Figure 1B:
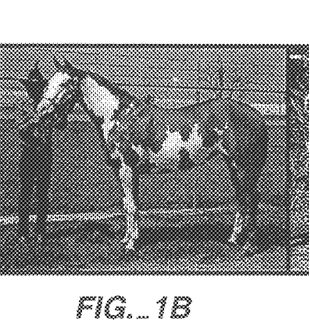
FIG. 1B shows a horse exhibiting a "frame" overo spotting pattern.
Figure 1C:
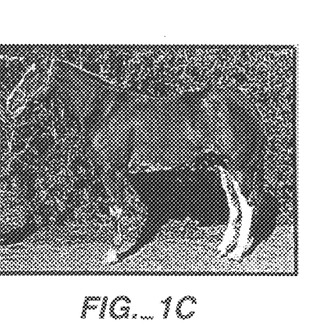
FIG. 1C shows a horse exhibiting an overo spotting pattern.

There are two distinct coat color patterns recognized by the American Paint Horse Association; tobiano and overo. Tobiano (FIG. 1A), inherited as an autosomal dominant trait, has been mapped to a linkage group containing Albumin and Vitamin D binding protein that is conserved in mouse and humans (Bowling, 1987). The overo inheritance pattern is not clearly defined and the map position has not been identified, perhaps because there are genetically different patterns registered as "overo". One particular pattern registered as overo is characterized by a variable pattern of jagged white markings predominantly localized to the lateral and ventral parts of the body, hence it is referred to as "frame" overo (FIG. 1B). Other patterns registered as overo exist where all four legs and the head are white but there is little white on the lateral aspect of the horse (FIG. 1C). Clear distinction between patterns is not always possible from phenotype so these patterns have been registered as a single category (overo). Frame overos are the specific subset of overos that most frequently appear to produce lethal white foals. McCabe et al., (1990); Trommershausen-Smith, (1977); Vonderfecht et al., (1983).

Lethal White Foal Syndrome is characterized by an all white coat and intestinal tract abnormalities that result in colic and related symptoms within 12 hours of birth in horses. The white coat is due to the absence of melanocytes from the skin. Although not all lethal white foals have been hearing tested, at least some of these foals are deaf and many have blue eyes in addition to the pigment defects and aganglionosis (McCabe et al., 1990; Trommershausen-Smith, 1977; Vonderfecht et al., 1983). Surgical intervention in Lethal White Foal Syndrome has not been successful. Therefore, this condition is lethal in all cases (McCabe et al., 1990).

A test or assay to genotype horses for Lethal White Foal Syndrome is of great interest to overo horse breeders. Such an assay could be used to identify horses that carry the lethal allele and therefore have a high risk for passing on the disease. Such an assay could also be used to identify horses that do not carry the lethal allele and hence will not produce lethal offspring.

The intestinal abnormalities resulting from Lethal White Foal Syndrome have been shown to be due to an absence of submucosal and myenteric neuronal plexi (enteric ganglia) that can extend from the jejunum to the rectum. It is not clear whether the pattern registered as overo in Paints is the result of alleles at a single locus or whether other loci may be involved.

The piebald mutation in mice produces a similar phenotype to overo and Lethal White Foal Syndrome. Homozygous piebald lethal mice are born white with an occasional head and/or rump patch. These mice are deaf 10% of the time and all have aganglionic megacolon which leads to death by three weeks of age. Lane J. Hered. 57:29–31 (1966). The molecular nature of this defect has been determined to be the absence of the EDNRB gene. In mouse mutants, the levels of transcript of this gene in lung corresponded to the amount of white spotting in the coat. Hosoda et al., Cell 79: 1267–1276 (1994).

Humans born with aganglionic megacolon have a condition called Hirschsprungs disease. The disease is characterized by the absence of intrinsic ganglion cells of both the myenteric and submucosal plexuses of the distal gastrointestinal tract. The result of this failure of innervation of the colon is delayed passage of the meconium, intestinal blockage and chronic severe constipation. The Endothelin-B Receptor has been shown to be responsible for susceptibility to Hirschsprungs disease in a Mennonite pedigree. In addition to megacolon, this extended family also had heterochromatic irises, deafness and hypopigmentation. Puffenberger, et al., Cell 79:1257–1266 (1994).

While there is much known about Hirschsprungs disease in humans and the piebald mutation in mice, it is not known what role, if any, the EDNRB gene might play in Lethal White Foal Syndrome in horses.

It is appreciated by those skilled in the art of molecular biological techniques that the cloning of the horse EDNRB gene and the identification of a specific mutation in the gene in horses suffering from Lethal White Foal Syndrome provides for the development of multiple molecular genetic tests for the identification, characterization and analysis of carriers of the gene for Lethal White Foal Syndrome.

The nucleotide sequences of the subject invention are used to detect differences in the sequences of genes that vary between normal horses and carriers of Lethal White Foal Syndrome. The nucleotide sequences of the subject invention are also utilized to determine expression of the Lethal White Foal Syndrome gene in various tissues.

Nucleotide sequences encoding a portion of a horse EDNRB gene and the gene product produced therefrom have numerous applications in techniques known to those skilled in the art of molecular biology. These techniques include use as PCR probes, use as hybridization probes, use in chromosome and gene mapping, use in the recombinant production of proteins encoded by the nucleotide sequence, generation of anti-sense RNA, DNA or nucleotide analogues and the like. The uses of the nucleotide sequences provided for in this application are exemplary of known techniques and are not intended to reflect any limitation on their use in any technique that would be known to the person of ordinary skill in the art. Furthermore, the nucleotide sequences provided for in this application may be used in molecular biology techniques that have not yet been developed, provided the new techniques rely on properties of polynucleotide sequences that are currently known to the person of average skill in the art, e.g., the triplet genetic code, specific base pair interactions, etc.

One aspect of this invention is the identification of the chromosomal location of the EDNRB gene in horses thereby enabling one of ordinary skill in the art to orient the horse genetic map with the mouse and human genetic maps. The nucleotide sequences provided herein may be mapped to chromosomes and specific regions of chromosomes using well-known genetic and/or chromosomal mapping techniques. These techniques include in situ hybridization, linkage analysis against known chromosomal markers, hybridization screening with libraries or flow-sorted chromosomal preparations specific to known chromosomes, and the like. Fluorescent in situ hybridization of chromosomal preparations and other physical chromosome mapping techniques, may be correlated with additional genetic map data. Examples of genetic map data can be found, for example, in *Genetic Maps: Locus Maps of Complex Genomes, Book 5: Human Maps*, O'Brien, editor, Cold Spring Harbor Laboratory Press (1990).

Nucleotide sequences encoding EDNRB genes may be joined to a variety of other nucleotide sequences of interest by means of well established recombinant DNA techniques (see, for example, Ausubel, et al., (1987).

Nucleotide sequences which are appropriate for joining to EDNRB sequences include an assortment of cloning vectors, e.g., plasmids, cosmids, lambda phage derivatives, phagemids, and the like, that are in the public domain. Vectors of interest include expression vectors, replication vectors, probe generation vectors, sequencing vectors, and the like. In general, vectors of interest may contain an origin of replication functional in at least one organism, convenient restriction endonuclease digestion sites, and selectable markers for the host cell.

Another aspect of the subject invention is to provide for EDNRB-specific nucleic acid hybridization probes capable of hybridizing with naturally occurring nucleotide sequences encoding EDNRBs. Nucleic acid hybridization probes for the detection of EDNRB encoding nucleotide sequences should preferably contain at least 50% of the nucleotides from the sequence of a given EDNRB encoding nucleotide sequence. The hybridization probes of the subject invention may be derived from the nucleotide sequences of the cDNA and the genomic sequences encoding EDNRBs uniquely identified by the nucleotide sequences of the EDNRB gene. Hybridization probes may be labeled by a variety of reporter groups, including fluorescent labels, radionuclides such as $^{32}P$ or $^{35}S$, or enzymatic labels such as alkaline phosphatase, coupled to the probe via avidin/biotin coupling systems, and the like.

An additional use for EDNRB probes involves their use as oligonucleotide primers for PCR, the polymerase chain reaction. Such PCR materials can be provided in the form of a kit. The kit may include all of the components necessary for carrying out the PCR analysis. Such components may include one or more oligonucleotide primers, PCR reaction buffer, DNA polymerase enzyme, gel electrophoresis analysis materials, directions for carrying out the PCR reactions, and the like. The polymerase chain reaction is described in detail in U.S. Pat. Nos. 4,965,188 and 4,683,195 and 4,800,195 which are hereby incorporated by reference. PCR techniques allow for the production of relatively large amounts of DNA for analysis of gene sequences, gene expression, etc. from small amounts of DNA. These techniques permit the differentiation between carriers and non-carriers of the Lethal White allele.

Probes for hybridization may be synthesized by both enzymatic and in vitro techniques. Short hybridization probes are preferably synthesized by in vitro methodology such as the use of commercially available DNA synthesizers like machines sold by Applied Biosystems (Foster City, Calif.). For example, nucleotide sequences of lengths greater than 10 base pairs may be produced by commercially available machines. Oligonucleotides produced by in vitro synthesis may be readily spliced together using generally known recombinant DNA techniques to produce a longer sequence of interest.

Other means of producing EDNRB-specific hybridization probes include the cloning of nucleic acid sequences encoding EDNRB derivatives into vectors for the production of RNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is also possible to produce a DNA sequence, or portions thereof, encoding EDNRB or EDNRB derivatives entirely by synthetic chemistry, after which the gene can be inserted into any of the many available DNA vectors using reagents, vectors and cells that are freely available and in the public domain at the time of the filing of this application. Synthetic chemistry may be used to reproduce the entire sequence of an EDNRB encoding gene, any portion thereof, or to introduce mutations into the sequence.

Nucleotide sequences encoding EDNRB sequence may be used to produce purified EDNRB protein or peptides using well-known methods of recombinant DNA technology. Among the many publications that teach methods for the expression of genes after they have been isolated is *Gene Expression Technology, Methods and Enzymology.* Vol.:185, edited by Goeddel, Academic Press, San Diego, Calif. (1990). EDNRB proteins or peptides may be expressed in a variety of host cells, or insert cells either prokaryotic or eukaryotic. Such cells can be microbial, mammalian, avian or plant cells. Preferably, host cells would be eukaryotic, more preferably host cells would be mammalian, most preferably host cells would be horse cells. Host cells may be from species either the same or different than the species from which the EDNRB encoding nucleotide sequences are naturally present, i.e., endogenous. Horse cells transfected with vectors expressing EDNRB encoding proteins can be used in gene therapy to treat horses with Lethal White Foal Allele Syndrome.

Cells transformed with expression vectors encoding EDNRB proteins may be cultured under conditions favoring expression of the EDNRB sequence and the recovery of the recombinantly-produced protein from the cell culture. An EDNRB produced by a recombinant cell may be secreted or may be contained intracellularly, depending on the particular genetic construction used. In general, it is more convenient to prepare recombinant proteins in secreted form. However, since EDNRB is an integral membrane protein, it will be more efficient to produce it intracellularly rather than secreting the protein. Purification steps will depend on the nature of the particular EDNRB produced.

Advantages of producing the EDNRB proteins or peptides by recombinant DNA technology include obtaining highly enriched sources of the proteins for purification and the availability of simplified purification procedures that permit rapid purification of large amounts of the protein.

In addition to recombinant production, EDNRB protein fragments may be produced by direct peptide synthesis using solid-phase techniques.

In vitro polypeptide synthesis may be performed using manual techniques or by automation. Automated synthesis may be achieved, for example, using Applied Biosystems 431A Peptide Synthesizer (Foster City, Calif.) following the instructions provided in the instruction manual supplied by the manufacturer.

Antibodies specific for EDNRB may be produced by using purified EDNRB protein or peptides for the induction of EDNRB-specific antibodies. By induction of antibodies it is intended not only the stimulation of an immune response by injection into animals, but analogous steps in the production of synthetic antibodies or other specific-binding molecules such as the screening of recombinant immunoglobulin libraries. Both monoclonal and polyclonal antibodies can be produced by procedures well known in the art.

Once isolated, a functional cDNA for EDNRB can be used for gene therapy in horses. Such functional DNAs can be transfected into horse cells for mutation complementation.

The examples below are provided to illustrate the subject invention. These examples are provided by way of illustration and are not included for the purpose of limiting the invention.

EXAMPLE 1

A. cDNA CLONING OF HORSE ENDOTHELIN-B RECEPTOR

A horse EDNRB cDNA clone was isolated and purified from a lung sample isolated from a solid colored horse. The procedure utilized was as follows:

1. Lung tissue from a horse without white in its coat (wild type) was collected and quickly frozen in liquid nitrogen and stored at −70° C.

2. RNA was isolated from this tissue using the Micro Fast Track mRNA isolation kit (Invitrogen, San Diego, Calif.)

3. First strand cDNA was synthesized from the mRNA using a cDNA synthesis kit from (Invitrogen, San Diego, Calif.).

4. Oligonucleotide primers were designed based on sequence conservation between bovine, mouse and human published sequences and gene structure for EDNRB. Arai, et al. (1990) Nature 348:730–735 and Saito et al., (1991) J. Biol. Chem 266:23433–37. Primer E1(ATG).F (5'-CAG GTA GCA GCA TGC AGC-3'), SEQ ID NO:1, contains the start codon and E7.R (5'-GGA ACG GAA GTT GTC ATA TCC-3'), SEQ ID NO:2, lies 21 nucleotides from the termination of the human sequence.

5. A 1303 base pair PCR product was amplified and cloned from first stand cDNA using the Tri-clone kit for mRNA isolation, RT-PCR and TA cloning (Invitrogen). The horse cDNA clone was sequenced using the fluorescent dideoxy terminator method from primers in the vector (M 13–40 and T7 primers) and two internal primers; E1.F (5'-GCA AAT GCC TAA AGC AGG GA-3'), SEQ ID NO:3 and E6.R (5'-GAT (GA)CC AAT (GT)TA GTC CAA TAC-3'), SEQ ID NO:4. The complete cDNA DNA sequence was determined and is presented in SEQ ID NO:20. The corresponding peptide sequence is presented in SEQ ID NO:21.

B. ISOLATION OF A HORSE ENDOTHELIN-B RECEPTOR GENOMIC CLONE

Primers were designed to amplify potential introns in the horse EDNRB gene based on inference from the gene structure in humans, Arai, et al., Nature 348:730–735 (1990). Four of the 6 introns of the horse EDNRB gene were amplified and directly sequenced.

The sequence of the introns allowed the generation of primers to amplify the exons from genomic DNA for analysis of the EDNRB gene in samples from foals with Lethal White Foal Allele Syndrome.

The following primers were used for Exon 1; E1 (ATG).F, SEQ ID NO:1 and E1.R (5'-TGC AGC A(GA) GTC TCC CAG AGC-3'), SEQ ID NO:5.

The following primers were used for Exon 2-Exon 3: E2.F (5'-CTG CT(TG) GC(TA) GAG GAC TGG CC-3'), SEQ ID NO:6 and E3.R (5'-CTG CAT GAA GGC TGT TTT CTG-3'), SEQ ID NO:7.

The following primers were used for Exon 4-Exon 5: E4.F (5'-CTA TTT CTG CTT GCC ATT GGC-3'), SEQ ID NO:8 and 15.R (5'CTC T(TC)T CTG CCT ATG AAA GGG-3'), SEQ ID NO:9

The following primers were used for Exon 6: 15.F (5'-GAA TGG AGA GCC AGA GAT GTC-3'), SEQ ID NO:10 and 16.R (5'-CAT CC(AG) TG(AG) TGT TAA TGC AAG GG-3'), SEQ ID NO:11.

The following primers were used for Exon 7: 16.F (5'-TGG AAA GAA AGT GGC CCA AG-3'), SEQ ID NO:12 and E7.R, SEQ ID NO:2.

The DNA sequences of the introns are presented in SEQ ID NO. 22 to SEQ ID NO. 25.

C. MAPPING

A horse somatic cell hybrid panel has been established by fusing horse fibroblasts with mouse cell lines to use as a syntenic mapping clone panel for horses.

Using this resource with primers specific for Intron 5 and Intron 6 of horse EDNRB, a synthetic cluster of 5 microsatellites (HMS25, HMS41, CA14, C031 and C077) and 2 RAPDs (Q6-550 and R15-1050) was identified and were referred to as UCD17.

EXAMPLE 2

A. SAMPLE ANALYSIS

A lung sample from a wild-type, solid-colored horse was obtained from the Veterinary Medical Teaching Hospital, Pathology Department (University of California, Davis). Blood samples from three lethal white foals used in the initial sequencing analysis were obtained from their owners. A group of 53 presumably unbiased, sequentially ordered Paint horses from the Veterinary Genetics Laboratory (VGL), University of California, Davis parentage testing program were used as an unselected panel. Two hair samples from viable white foals and their sires and dams, neither of whom was a frame overo, were submitted by their owners. Two samples were tested from foals with white spotting patterns similar to overo that were the product of Quarter horse parents (cropout).

The blood samples were processed after centrifugal separation of the white blood cells (Ausubel, 1987). DNA was extracted from the hair samples by incubating 4 hair roots in 50 µl of 200 mM HCl, 100 mM Tris-HCI pH 8.5. The samples were then extracted with phenol/chloroform/isoamyl alcohol and ethanol precipitated. The DNA was then resuspended in 20 µl distilled water. One µl of the resuspended DNA was used for subsequent PCR reactions.

Primers E1.F (SEQ ID NO: 3) and E1.R (SEQ ID NO: 5) were used to PCR amplify genomic DNA from hair and blood samples for subsequent analysis and sequencing. The primer used for sequencing was E1–2.F (5'-GAA CCA TCG AGA TCA AUG AGA C-3'), SEQ ID NO: 13.

An assay was developed to evaluate the presence of the lethal white associated allele using allele specific PCR primers: lw2.F (5'-CAT CAA GGG AAA CTC CAC AC-3'), SEQ ID NO: 14 and wt2.F (5'-GTG TGG AGT TTC CGA TGA TG-3'), SEQ ID NO: 15. PCR conditions were as follows for blood and tissue samples using 100 ng of DNA per reaction: 12 minutes at 94° C. followed by 35 cycles of 5 seconds at 94° C., 10 mins at 58° C., 30 seconds at 72° C. for 35 cycles using 1 uM of primers E1–2.F, lw2.F, wt2.F, and E1.R (SEQ ID. NO: 13, 14, 15, 5).

Nested PCR conditions were necessary on the hair samples.

The following conditions were used: 12 minutes at 94° C., followed by 10 cycles of 10 seconds at 94° C., 15 seconds at 55° C., 30 seconds at 72° C. using 1 μM of primers E1.F and E1.R. (SEQ ID NO: 3 and SEQ ID NO: 7). Two μl of the first PCR reaction was added to the second reactions and the following PCR conditions were utilized: 12 minutes at 94° C., followed by 30 cycles of 5 seconds at 94° C., 10 seconds at 58° C., 30 seconds at 72° C. using 0.5 uM of primers E1–2.F, lw2.F, wt2.F, E1.R, (SEQ ID NOS.: 13, 14, 15, 5). All PCR 1 5 reactions were carried out in a Perkin-Elmer Cetus 9600 Thermal-Cycler in a total volume of 20 ul containing 1×PCR buffer with 1.5 mM $MgCl_2$ (Perkin-Elmer), 0.1 ul of Taq-gold (Perkin-Elmer), and 0.1 mM dNTP.

The PCR reaction products were run on a 12% polyacrylamide 20 gel and stained with ethidium bromide for the subsequent visualization of the products. A 174 bp positive control for PCR reaction is present in all lanes. A 105 bp lethal white allele product and a 90 bp wildtype allele product can be distinguished on a 12% polyacrylamide gel (see FIG. 2B). Thus, carriers of the Lethal White Foal Allele can easily be identified by PCR.

B. SEQUENCE RESULTS

The PCR reaction products were sequenced. A two base pair change was identified in the lethal white samples as compared to the wildtype sample. The identified mutation is a TC to AG change (nucleotide 352, 353) that results in an amino acid change of isoleucine to lysine (Amino acid 118) in the first transmembrane domain of the horse endothelin-B receptor. Further testing of horse samples demonstrated that 7 lethal white foals carried this allele, whereas 14 wild-type samples did not.

The sequence results were as follows:

| Wild-Type | | | | | |
|---|---|---|---|---|---|
| DNA sequence | GGC | ATC | ATC | GGA | AAC |
| Amino acid sequence | G | I | I | G | N |
| Lethal White | | | | | |
| DNA sequence | GGC | ATC | AAG | GGA | AAC |
| Amino acid sequence | G | I | K | G | N |

These sequences are presented in SEQ ID NO: 16 to 19.

C. SCHEMATIC REPRESENTATION OF THE MUTATION

Figure 3:
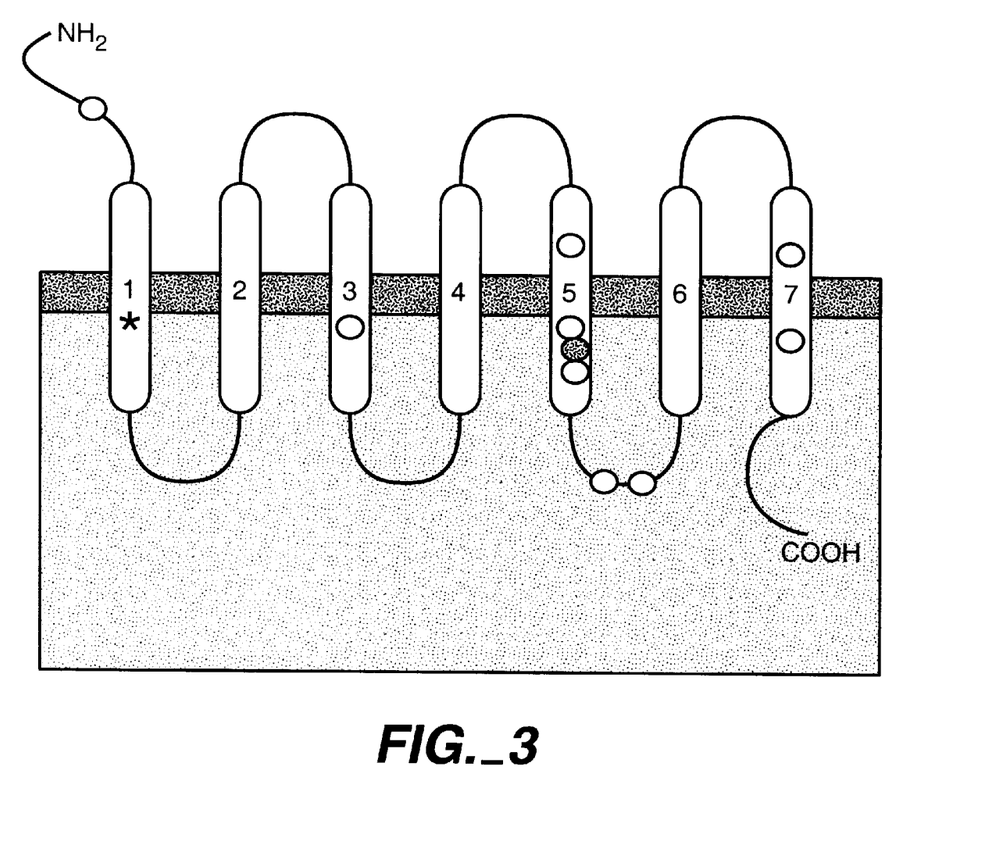

FIG. 3 shows a schematic diagram of the endothelin-B receptor protein and the above sequence results. The gray area represents the plasma membrane. The cylinders numbered 1–7 represent the transmembrane domain of the EDNRB protein. An asterisk marks the location of missense mutation in the horse EDNRB protein. Open circles mark the location of the missense mutations in the human EDNRB protein. The closed circle marks the location of the missense mutation identified in the mice EDNRB protein. The missense mutation in the horse EDNRB protein is in a completely different and unexpected location in the EDNRB sequence as compared to the mouse and human EDRRB sequences.

EXAMPLE 3

GENOTYPING OF HORSES

Figure 2A:
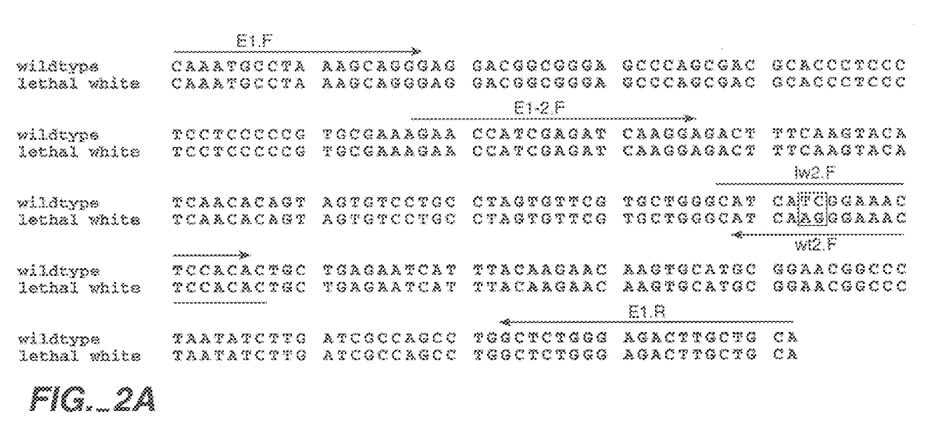
FIG. 2A shows the orientation and position of primers used in a polymerase chain reaction (PCR) assay to detect the two base pair mutation associated with Lethal White Foal Syndrome. Arrows indicate the 3' end of each primer. The box is placed around the two base pair sequence difference between wild-type horse and lethal white horse DNA.

An allele specific PCR assay was developed to analyze the EDNRB allele in the Paint Horse population and in other breeds. This assay utilizes four primers which produce three PCR products in a PCR reaction of a sample from a heterozygote. Two outer primers (E1.F and E1.R), (SEQ ID NO: 3, SEQ ID NO: 5) amplified a 174 bp fragment that serves as a positive control for the PCR reaction. One of the outer primers and the wild-type allele-specific primer (E1.2.F and wt2.F), (SEQ ID NO: 13, SEQ ID NO: 15) amplifies a 90 bp fragment and the other outer primer and the lethal white specific primer (E1.R and lw2.F), (SEQ ID NO: 5, SEQ ID NO: 14) amplifies a 105 bp fragment. See FIG. 2.

The PCR conditions were as follows: blood and tissue samples (100 ng of DNA per reaction): 12 minutes at 94° C., followed by 35 cycles of 5 seconds at 94° C., 10 seconds at 58° C., 30 seconds at 72° C. using 1 μM of primers E1–2.F, lw2.F, wt2.F, and E1.R, (SEQ ID NO: 13, 14, 15, 5).

Nested PCR conditions were necessary on the hair samples. The following conditions were used; 12 minutes at 94° C., followed by 10 cycles of 10 seconds at 94° C., 15 seconds at 55° C., 30 seconds at 72° C. using 1 μM of primers E1.F, (SEQ ID NO: 3) and E1.R, (SEQ ID NO: 2).

Figure 2B:
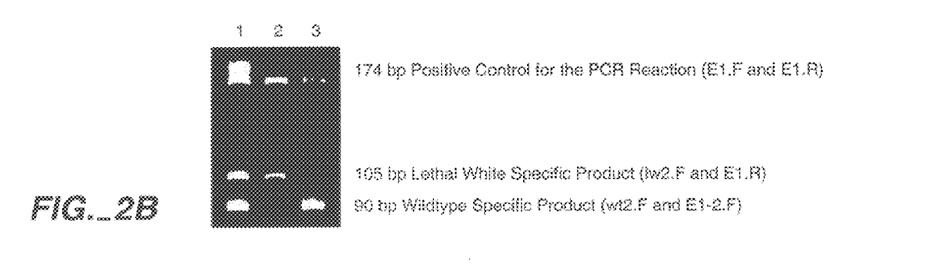

Two μl of the first PCR reaction was added to the second reaction and a second PCR reaction was carried out with the following conditions: 12 minutes at 94° C., followed by 30 cycles of 5 seconds at 94° C., 10 seconds at 58° C., 30 seconds at 72° C. using 0.5 uM of primers E1–2.F, lw2.F, wt2.F, E1.R (SEQ ID NO: 13, 14, 15, 5). All PCR reactions were carried out in a Perkin-Elmer Cetus 9600 thermal cycler in a total volume of 20 μl containing 1×PCR buffer with 1.5 mM $MgCl_2$ (Perkin-Elmer), 0.1 μl of Taq-gold (Perkin-Elmer), and 0.1 mM dNTP. The PCR products were visualized on 12% polyacrylamide gel run stained with ethidium bromide as shown in FIG. 2B.

The integrity of the assay was monitored by sequencing 50 alleles of the 38 tested and demonstrating that the DNA sequence results always corresponded to the PCR assay results.

Samples from 138 horses were genotyped using the allele specific PCR assay for the EDNRB gene. The results are shown in Table 1.

In Table 1, horse breed and coat pattern are listed in the left column. The number of animals of each genotype is listed in the right columns. The wildtype allele is indicated by "+" and "lw" indicates the mutant lethal white allele.

Frame overo is a particular coat pattern registered as overo by the American Paint Horse Association (APHA). Tobiano and Tob/overo are the other patterns recognized by the APHA. Paint horses not marked with sufficient white coloring are registered as breeding stock by APHA. Crop-outs are spotted foals of American Quarter horses (eligible for registration by APHA). Viable whites are foals born all white without aganglionic megacolon.

The samples obtained from foals with Lethal White Foal Syndrome were the only homozygotes identified. All frame overos 42/42 tested were heterozygous for the mutation. Fourteen of the frame overos were parents of foals with Lethal White Foal Syndrome.

Two of the quarter horse samples were particularly selected because the horses had produced spotted foals (cropouts). These two horses were heterozygotes although they were solid colored. In addition, one breeding stock (paints that do not have enough white spotting to be fully registered) sample was a heterozygote. The thoroughbred sample is a frame overo horse that sired a lethal white foal.

The result that all frame overo horses were heterozygous for the mutation associated with Lethal White Foal Syndrome explains why lethal white foals are produced predominantly by frame overos. The data supports the model that Lethal White Foal Syndrome is caused by homozygosity for a mutation in the EDNRB gene of horses and that horses heterozygous for this mutation generally display the frame overo phenotype (if a spotted phenotype is manifested).

The Paint horse breed registers certain white-marked foals born of Quarter Horse or Thoroughbred parents. This practice allows mutations that arise in these two breeds that affect coat pattern to be maintained instead of being eliminated from the gene pool. Considering the foundation of the breed it was surprising that there was only one mutation responsible for Lethal White Foal Syndrome. There was no evidence that another gene is responsible for Lethal White Foal Syndrome.

Lethal White Foal Syndrome provides a new animal model for Hirschsprungs Disease. Although there are similarities between Lethal White Foal Syndrome and the human disease there are also several differences. In horses, the melanocyte defect is apparent in heterozygotes, while in humans the melanocyte defect (hypopigmentation) is seen only in homozygotes. Humans that are heterozygous for a mutation in EDNRB can have aganglionic megacolon whereas heterozygous horses do not. Bicolored irises and deafness are two traits that have been seen in human patients homozygous for mutations in this gene. Chakravarti, Hum. Mol. Genet. 5:303–307, (1996); Puffenberger et al., Cell 79:1257–1266, (1994). These traits exist in the Paint horse as well.

The present invention now provides a means to test Paint Horses for carrier status of the Lethal White Foal Syndrome-associated allele. At the simplest level of genetic testing, it appears that any cross between two frame overos is destined to produce 1/4 of the offspring with Lethal White Foal Syndrome, 1/2 frame overo and 1/4 wild-type (solid). The molecular test can also identify carriers that cannot be recognized by overt phenotype. For example, some tobiano Paint horses, Quarter Horses and Thoroughbreds are carriers. The widespread use of this test could lead to the elimination of this disease from the horse population while allowing breeders to produce heterozygous animals with the valued spotting pattern. In addition, the use of the tests of the present invention will permit breeders to accurately determine if horses are carriers of the gene and avoid the previous problems of misdiagnosis in certain cases. For example, white foals born of Paint horse parents should not be immediately euthanized since unless they are tested or show symptoms of colic they may not have aganglionosis as they may not contain the mutation.

TABLE 1

| Horse Breeds and Coat Pattern | GENOTYPE | | |
|---|---|---|---|
| | +/+ | +/lw | lw/lw |
| Registered Paints | | | |
| Frame overo | | 36 | |
| Non-frame overo | 6 | | |
| Tobiano | 20 | 1 | |
| Tob/overo | 3 | 2 | |
| Solid (breeding stock) | 6 | 1 | |
| Lethal white | | | 10 |
| Viable white | 2 | | |
| Registered Quarter horse | | | |
| solid | 17 | 2[a] | |
| American Miniature | | | |
| overo | | 3 | |
| lethal white | | | 1 |
| solid | | 1 | |
| Cropout (Quarter Horse Parents) | | 2 | |
| Other breeds | | | |
| Thoroughbred | 7 | 1[a,b] | |
| Arabian | 11 | | |
| Morgan | 3 | | |
| Lipizzaner | 1 | | |
| Paso Fino | 2 | | |
| Tobiano pony | 1 | | |
| (frame overo) | | 1 | |
| unknown | 3 | | |
| Subtotal | 82 | 50 | 11 |
| Total | | 143 | |

[a] Animals were selected because they had produced a spotted or lethal white foal.
[b] This horse was a frame overo.

We claim:

1. An isolated oligonucleotide consisting of a nucleotide sequence selected from the group consisting of:
   SEQ ID NO: 2, the complement of SEQ ID NO: 2, SEQ ID NO: 3, the complement of SEQ ID NO: 3, SEQ ID NO: 5, the complement of SEQ ID NO: 5, SEQ ID NO: 13, the complement of SEQ ID NO: 13, SEQ ID NO: 14 and the complement of SEQ ID NO: 14, SEQ ID NO: 15 and the complement of SEQ ID NO: 15.

2. The oligonucleotide of claim 1 wherein the nucleotide sequence is SEQ ID NO: 2.

3. The oligonucleotide of claim 1 wherein the nucleotide sequence is SEQ ID NO: 3.

4. The oligonucleotide of claim 1 wherein the nucleotide sequence is SEQ ID NO: 5.

5. The oligonucleotide of claim 1 wherein the nucleotide sequence is SEQ ID NO: 13.

6. The oligonucleotide of claim 1 wherein the nucleotide sequence is SEQ ID NO: 14.

7. The oligonucleotide of claim 1 wherein the nucleotide sequence is SEQ ID NO: 15.

8. An isolated nucleic acid consisting of a nucleotide sequence shown in SEQ ID NO: 20.

9. An isolated nucleic acid consisting of the coding for the polypeptide of SEQ ID NO: 21.

10. The nucleic acid of claim 8 wherein said nucleic acid is linked to a heterologous nucleic acid.

11. A nucleic acid construct of claim 10 wherein said heterologous nucleic acid is a promoter.

12. The nucleic acid construct of claim 11 wherein said promoter is functional in a cell selected from the group consisting of mammalian cells, microbial cells, avian cells and plant cells.

13. The nucleic acid construct of claim 10 wherein said heterologous nucleic acid is vector.

14. The nucleic acid construct of claim 13 wherein said vector is functional in a cell selected from the group consisting of mammalian cells, microbial cells, avian cells and plant cells.

15. An isolated oligonucleotide consisting of a sequence selected from the group consisting of SEQ ID NO: 1, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 16, SEQ ID NO: 18, SEQ ID NO: 22, SEQ ID NO: 23, SEQ ID NO: 24 and SEQ ID NO: 25 and the complement of SEQ ID NO's: 1, 4, 6–12, 16, 18 and 22–25.

16. The oligonucleotide of claim 15 wherein the sequence is SEQ ID NO: 25.

17. The oligonucleotide of claim 15 wherein the sequence is SEQ ID NO: 24.

18. The oligonucleotide of claim 15 wherein the sequence is SEQ ID NO: 23.

19. The oligonucleotide of claim 15 wherein the sequence is SEQ ID NO: 22.

* * * * *

SEQUENCE LISTING

<160> NUMBER OF SEQ ID NOS: 25

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide primer sequence based on
      sequence conservation between bovine, mouse and human published sequences and gene structure for endothelin-B receptor.

<400> SEQUENCE: 1
caggtagcag catgcagc                                              18

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer for EXON 7 amplification
      and PCR analysis of Lethal White Foal Allele.

<400> SEQUENCE: 2
ggaacggaag ttgtcatatc c                                          21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Internal
      primer for DNA sequencing.

<400> SEQUENCE: 3
gcaaatgcct aaagcaggga                                            20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Internal
      primer for DNA sequencing horse EDNRB cDNA.

<400> SEQUENCE: 4
gatrccaatk tagtccaata c                                          21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 1 and PCR analysis of Lethal White
      Foal Allele.

<400> SEQUENCE: 5
tgcagcargt ctcccagagc                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 2-EXON 3.

<400> SEQUENCE: 6
ctgctkgcwg aggactggcc                                            20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:Primer for DNA sequencing horse EDNRB EXON 2-EXON 3.

<400> SEQUENCE: 7
ctgcatgaag gctgttttct g                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 4-EXON 5.

<400> SEQUENCE: 8
ctatttctgc ttgccattgg c                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 4-EXON 5.

<400> SEQUENCE: 9
ctctytctgc ctatgaaagg g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 6.

<400> SEQUENCE: 10
gaatggagag ccagagatgt c                                              21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 6.

<400> SEQUENCE: 11
catccrtgrt gttaatgcaa ggg                                            23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Primer for
      DNA sequencing horse EDNRB EXON 7.

<400> SEQUENCE: 12
tggaaagaaa gtggcccaag                                                20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:Primer for
      DNA sequencing horse EDNRB PCR products.

```
<400> SEQUENCE: 13
gaaccatcga gatcaagaga c                                        21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Primer for
      horse EDNRB PCR analysis.

<400> SEQUENCE: 14
catcaaggga aactccacac                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Primer for
      horse EDNRB PCR analysis.

<400> SEQUENCE: 15
gtgtggagtt tccgatgatg                                          20

<210> SEQ ID NO 16
<211> LENGTH: 15
<212> TYPE: DNA
<213> ORGANISM: Horse
<220> FEATURE:
<223> OTHER INFORMATION: Horse EDNRB DNA Sequence.

<400> SEQUENCE: 16
ggcatcatcg gaaac                                               15

<210> SEQ ID NO 17
<211> LENGTH: 5
<212> TYPE: PRT
<213> ORGANISM: Horse
<220> FEATURE:
<223> OTHER INFORMATION: Horse EDNRB Protein Sequence.

<400> SEQUENCE: 17

Gly Ile Ile Gly Asn
 1               5

<210> SEQ ID NO 18
<211> LENGTH: 15
<212> TYPE: DNA
<213> ORGANISM: Horse
<220> FEATURE:
<223> OTHER INFORMATION: Horse EDNRB DNA Sequence.

<400> SEQUENCE: 18
ggcatcaagg gaaac                                               15

<210> SEQ ID NO 19
<211> LENGTH: 5
<212> TYPE: PRT
<213> ORGANISM: HORSE

<400> SEQUENCE: 19

Gly Ile Lys Gly Asn
 1               5
```

<210> SEQ ID NO 20
<211> LENGTH: 1321
<212> TYPE: DNA
<213> ORGANISM: Horse

<400> SEQUENCE: 20

| | | | | | |
|---|---|---|---|---|---|
| caggtagcag | catgcagcct | ctgccaaccc | tgtgtggacg | cgttctggtg | gcgctgatcc | 60 |
| ttgcctgcgg | cgtggcaggg | gtccagggag | aagagaggag | attcccgccg | gccagggcca | 120 |
| ctccgccact | tctggggtct | gaagagataa | tgacgcccc | gactaagacc | tcctggccga | 180 |
| cggggtccaa | cgccagcgtg | ccgcggtcat | cagcacctcc | gcaaatgcct | aaagcaggga | 240 |
| ggacggcggg | agcccagcga | cgcaccctcc | ctcctccccc | gtgcgaaaga | accatcgaga | 300 |
| tcaaggagac | tttcaagtac | atcaacacag | tagtgtcctg | cctagtgttc | gtgctgggca | 360 |
| tcatcggaaa | ctccacactg | ctgagaatca | tttacaagaa | caagtgcatg | cggaacggcc | 420 |
| ctaatatctt | gatcgccagc | ctggctctcc | gagacctgct | gcaaatcatc | attgacgtcc | 480 |
| ccatcaatgt | ctacaagctg | ctggctgagg | actggccctt | tggagtcgag | atgtgtaagc | 540 |
| tggtgccttt | catacagaag | gcctccgtgg | gcatcactgt | gctgagtctg | tgtgctctaa | 600 |
| gtattgacag | atatcgagct | gttgcttcct | tggagcgaat | taaggaatt | cgggttccaa | 660 |
| aatggacagc | agtagaaatt | gttttaattt | gggtggtctc | tgtggttctg | gctgtccctg | 720 |
| aagccgtggg | ttttgatatg | attaccgctg | actacaaagg | aagttatctg | cgaatctgcc | 780 |
| tgcttcatcc | cactcagaaa | acagccttca | tgcagtttta | caagaatgct | aaggactggt | 840 |
| ggctatttag | tttctatttc | tgcttgccat | tggccatcac | tgcatttttt | tataccttga | 900 |
| tgacctgtga | aatgttgaga | aagaagagtg | gcatgcaaat | tgctttaaat | gatcacttaa | 960 |
| agcagagaag | ggaagtggcg | aaaacagtat | tctgcctggt | ccttgtcttt | gccctgtgct | 1020 |
| ggcttcctct | tcacctcagc | aggattttga | aacacactct | ttatgatcag | aatgatcccc | 1080 |
| atagatgtga | actttgagc | tttttgttgg | tattggacta | cattggcatc | aacatggcct | 1140 |
| ccctgaattc | ctgcattaat | ccaatagctc | tgtatttggt | gagcaaaaga | ttcaaaaact | 1200 |
| gctttaagtc | gtgcttatgc | tgctggtgcc | aatcatttga | agaaaaacag | tccttggaag | 1260 |
| acaagcagtc | atgcttaaag | ttcaaagcta | atgatcacgg | atatgacaac | ttccgttcca | 1320 |
| a | | | | | | 1321 |

<210> SEQ ID NO 21
<211> LENGTH: 436
<212> TYPE: PRT
<213> ORGANISM: HORSE
<220> FEATURE:
<223> OTHER INFORMATION: Horse EDNRB cDNA Peptide Sequence.

<400> SEQUENCE: 21

Met Gln Pro Leu Pro Thr Leu Cys Gly Arg Val Leu Val Ala Leu Ile
1               5                   10                  15

Leu Ala Cys Gly Val Ala Gly Val Gln Gly Glu Glu Arg Arg Phe Pro
            20                  25                  30

Pro Ala Arg Ala Thr Pro Pro Leu Leu Gly Ser Glu Glu Ile Met Thr
        35                  40                  45

Pro Pro Thr Lys Thr Ser Trp Pro Thr Gly Ser Asn Ala Ser Val Pro
    50                  55                  60

Arg Ser Ser Ala Pro Pro Gln Met Pro Lys Ala Gly Arg Thr Ala Gly
65                  70                  75                  80

-continued

```
Ala Gln Arg Arg Thr Leu Pro Pro Pro Cys Glu Arg Thr Ile Glu
                 85                  90                  95

Ile Lys Glu Thr Phe Lys Tyr Ile Asn Thr Val Val Ser Cys Leu Val
            100                 105                 110

Phe Val Leu Gly Ile Ile Gly Asn Ser Thr Leu Leu Arg Ile Ile Tyr
        115                 120                 125

Lys Asn Lys Cys Met Arg Asn Gly Pro Asn Ile Leu Ile Ala Ser Leu
130                 135                 140

Ala Leu Arg Asp Leu Leu Gln Ile Ile Ile Asp Val Pro Ile Asn Val
145                 150                 155                 160

Tyr Lys Leu Leu Ala Glu Asp Trp Pro Phe Gly Val Glu Met Cys Lys
                165                 170                 175

Leu Val Pro Phe Ile Gln Lys Ala Ser Val Gly Ile Thr Val Leu Ser
            180                 185                 190

Leu Cys Ala Leu Ser Ile Asp Arg Tyr Arg Ala Val Ala Ser Leu Glu
        195                 200                 205

Arg Ile Lys Gly Ile Arg Val Pro Lys Trp Thr Ala Val Glu Ile Val
210                 215                 220

Leu Ile Trp Val Val Ser Val Val Leu Ala Val Pro Glu Ala Val Gly
225                 230                 235                 240

Phe Asp Met Ile Thr Ala Asp Tyr Lys Gly Ser Tyr Leu Arg Ile Cys
                245                 250                 255

Leu Leu His Pro Thr Gln Lys Thr Ala Phe Met Gln Phe Tyr Lys Asn
            260                 265                 270

Ala Lys Asp Trp Trp Leu Phe Ser Phe Tyr Phe Cys Leu Pro Leu Ala
        275                 280                 285

Ile Thr Ala Phe Phe Tyr Thr Leu Met Thr Cys Glu Met Leu Arg Lys
290                 295                 300

Lys Ser Gly Met Gln Ile Ala Leu Asn Asp His Leu Lys Gln Arg Arg
305                 310                 315                 320

Glu Val Ala Lys Thr Val Phe Cys Leu Val Leu Val Phe Ala Leu Cys
                325                 330                 335

Trp Leu Pro Leu His Leu Ser Arg Ile Leu Lys His Thr Leu Tyr Asp
            340                 345                 350

Gln Asn Asp Pro His Arg Cys Glu Leu Leu Ser Phe Leu Leu Val Leu
        355                 360                 365

Asp Tyr Ile Gly Ile Asn Met Ala Ser Leu Asn Ser Cys Ile Asn Pro
370                 375                 380

Ile Ala Leu Tyr Leu Val Ser Lys Arg Phe Lys Asn Cys Phe Lys Ser
385                 390                 395                 400

Cys Leu Cys Cys Trp Cys Gln Ser Phe Glu Glu Lys Gln Ser Leu Glu
                405                 410                 415

Asp Lys Gln Ser Cys Leu Lys Pro Lys Ala Asn Asp His Gly Tyr Asp
            420                 425                 430

Asn Phe Arg Ser
        435

<210> SEQ ID NO 22
<211> LENGTH: 511
<212> TYPE: DNA
<213> ORGANISM: Horse
<220> FEATURE:
<223> OTHER INFORMATION: Uncertain of the nucleotide sequence at
      positions
<223> OTHER INFORMATION: 1, 7, 19, 21, 38, 381, 430, 434, 442, 444 and
      502.
```

<400> SEQUENCE: 22

```
nttctantcg catttttttnc naccttgatg acctgtgnaa atgttgagaa agaagagtgg      60
catgcaaatt gctttaaatg atcacttaaa gcaggtaaga aaatagaaat atgtactaag     120
gcatgattac aattatggtt aggaataaga aaattattgt gatgataaca aactaaaata     180
attatatacc aaagcatatt tcccttcctt gcttctggta tttttgaata tacacgggat     240
attttttata ttatctatct agagatattc tatataacct aaaaggatct agaaagagcc     300
attacttatt aagaatgagt ctctagttat ttgagttcta attcacatta actatttaat     360
ttgaagctca ttggtcctga nttttttacaa atgccactga cttttttgtaa agcagtgtta    420
actgttctgn ttancaaggg anantgccgt gattataacg aaccatttat tgagtgtctg     480
gctgtggttt tatttcagaa anggaattca c                                    511
```

<210> SEQ ID NO 23
<211> LENGTH: 752
<212> TYPE: DNA
<213> ORGANISM: Horse
<220> FEATURE:
<223> OTHER INFORMATION: Uncertain of the nucleotide sequence at
      positions
<223> OTHER INFORMATION: 2, 18, 19, 23, 30, 35, 55, 567, 698 and 733.

<400> SEQUENCE: 23

```
anatttaagc tatttggnnc ganttaaacn aatantcaag ctgatccatc aagcntggta      60
ccgagctcgg atccactagt aacggccgcc agtgtgctgg aattcggctt gatgccaatg     120
tagtccaata ccaacaaaaa gctgtaaaaa agcccaaaa catgtctgtg aaaaatatgc      180
tgctctgagc atgtattctt tgcagacttt tgtgttttttg tgaagaaaaa aattactgat   240
aacaatagtt ttgactttct cactggcctt tgctgataat aattcctctc tctcttcctc    300
tctgcctggc tctctctttc tctcattctc tgtcgttgcc caccctccac cccttgccc    360
agttctctct tttaaaataa aatctcattt ggaantgctg aggctggctg aaagaaggat    420
ttacaaagtg tagagaagaa tcagacctga tgttttcaat catgctattg actcatcatt   480
ttgacaactc tggcgctcca tttccagggt tcttataagt cccctttact ccttcgtcta    540
aaataggagc gaaagtaaaa aaaggganaat cttaattgct ccttaaggga ttagaaaagt   600
aatacctct ctttctgcct atgaaagggg ttaatggaaa aacttctgaa tggcattatt     660
tacaatacaa ttctattttta cctttcttac ctcaaaantc acatctatgg ggatcatcta    720
agccgaattc gcanatatcc atcaactggc gc                                   752
```

<210> SEQ ID NO 24
<211> LENGTH: 744
<212> TYPE: DNA
<213> ORGANISM: Horse
<220> FEATURE:
<223> OTHER INFORMATION: Uncertain of the nucleotide sequence at
      positions
<223> OTHER INFORMATION: 7, 13, 361, 512, 544, 545, 563, 602, 639, 659,
<223> OTHER INFORMATION: 677, 678, 706, 721, 734, 735 and 739.

<400> SEQUENCE: 24

```
tccgcangta ccnaggtgac actatagaat atcaagctat gcatcaagct tggtaccgag      60
ctcggatcca ctagtaacgg ccgccagtgt gctggaattc ggctttggct ctgtatttgg     120
tgagcaaaag attcaaaaac tgctttaagg taagagtttt ccaaaatgaa aagctcccctt    180
taatctggca ccaaatgtaa cccttccaaa ctattaatat ttctatccag agagatctag     240
```

```
taaattgttt tacattttcc cttgcattac atcatggatg attttntaaa atatgacttt      300
tgntcataaa tcactatagt tgatttctgc ctataaatct tagtcaacca ctccctgctg      360
nctcaaccaa tcagttataa acatagaatt gttaataaaa ttaataaaaa ttacatgcat      420
tgatatctga cagatatcac ataataaaat aagagctaaa acatgaatta aatacactgt      480
ttctgttttg ggtggatttg ggactatgca gnacaatttg gattatagtt aagttgggtc      540
tctnntcaca tggacataag atnacaagac agcaaagaat tttttcaagt ctcctctctt      600
tncaccttgg taagcagaga tgtgtcccng agtggatatg tgaatatctc cgtcaatgnt      660
gctggtatac caccacnntc ctcatctcaa aatttaatga atgatntccc tcctattggg      720
nacttttgcc cggnnccana ttgc                                             744
```

```
<210> SEQ ID NO 25
<211> LENGTH: 801
<212> TYPE: DNA
<213> ORGANISM: Horse
<220> FEATURE:
<223> OTHER INFORMATION: Uncertain of the nucleotide sequence at
      positions
<223> OTHER INFORMATION: 30, 54, 286, 436, 445, 542, 614, 617, 624, 641,
<223> OTHER INFORMATION: 731, 746, 753, 770, 775 and 793.

<400> SEQUENCE: 25
ttgcatacga tcctatagag cgaattgggn cctctagatg catgctcgag cggncgccag       60
tgtgatggat atctgcagaa ttcggcttgg aacggaagtt gtcatatccg tgatcattag      120
ctttgaactt taagcatgac tgcttgtctt ccaaggactg ttttcttca aatgattggc       180 accagcagca taagcacgac tgtacaaaac aaataactcg tttatatgtt tacatcagtt      240
acactgtcat gaccttcct actttctagg gttctgactt tctttgnatg atccagaatt       300
cttgggccac tttcttcca cgctctctta tttttctcct taaaaacata taattacaca      360
agtagtatat gacaattttt ttaaactaga aaatacagag aagaaaaaaa tgtatataat      420
taaaatactt cacctnttaa ttaanattaa agagaaagt cactcttaat tcttgatatt      480 taccctttgga ttacttaaga aatactctta atacttggat aaatatttta actcaagacc     540
tnttatattg caaaatagga aatatgacca cacacataca tttacatgac ttgttttttgt     600 gcatgttggg gggnagnaat gtgntttaat ctatttcaat naaaattggt atacatacta     660
actcccatag gatgcttttt ctcacttgan agggtcaata acaccccca tgtcaatgag      720 gtttacaata naatggccat cttttncaag canaatgtta tctcaangtn ccctncaagg     780
tttggtatca aanaagatcc c                                                801
```